United States Patent
Rietz et al.

(10) Patent No.: US 6,380,445 B1
(45) Date of Patent: Apr. 30, 2002

(54) POLY(9,9'-SPIROBISFLUORENES), THEIR PRODUCTION AND THEIR USE

(75) Inventors: Ralf-Roman Rietz; Wolfgang Wernet, both of Kobe (JP)

(73) Assignee: Vantico Inc., Brewster, NY (US)

( * ) Notice: Subject to any disclaimer, the term of this patent is extended or adjusted under 35 U.S.C. 154(b) by 0 days.

(21) Appl. No.: 09/567,348

(22) Filed: May 9, 2000

Related U.S. Application Data

(63) Continuation of application No. 09/077,484, filed as application No. PCT/EP96/05091 on Nov. 19, 1996, now Pat. No. 6,132,641.

(30) Foreign Application Priority Data

Jan. 12, 1995 (CH) ................................. 3411/95

(51) Int. Cl.[7] .................. C07C 25/22; C07C 25/18; C07C 17/02; C07C 311/00
(52) U.S. Cl. .................. 570/129; 570/183; 570/190; 558/46
(58) Field of Search ................. 570/129, 183, 570/190; 558/46

(56) References Cited

U.S. PATENT DOCUMENTS

| | | | |
|---|---|---|---|
| 5,026,894 A | 6/1991 | Tour et al. | 528/12 |
| 5,621,131 A | 4/1997 | Kreuder et al. | 558/46 |

FOREIGN PATENT DOCUMENTS

| | | |
|---|---|---|
| EP | 0676461 | 10/1995 |
| EP | 0707020 | 4/1996 |
| JP | 4221328 | 8/1992 |
| WO | 90/13148 | 11/1990 |

OTHER PUBLICATIONS

Adv. Mater., vol. 6, No. 3, (1994), pp. 190–198.
Derwent Publications AN 313655 for JP 4 221 328, Aug. 11, 1992.
Tetrahedron Lett., vol. 32, No. 39, (1991), pp. 5309–5312.
Chem. Abstr. 116:41262.
ISR. J. Chem., vol. 32, No. 1, (1992), pp. 69–77.
Chem. Abstr., 118:233206.
Macromolecules, vol. 25, No. 4, (1992), pp. 1214–1223.
Chem. Abstr. 113:192072.
Polymer Prepr. (Am. Chem. Soc., Div. Polym. Chem.), vol. 31, No. 1, (1990), pp. 408–409.

*Primary Examiner*—Tae H. Yoon
(74) *Attorney, Agent, or Firm*—Lyon & Lyon LLP

(57) ABSTRACT

Soluble poly(bis-9,9'-fluorenes) comprise identical or different structural repeating units of the formula I,

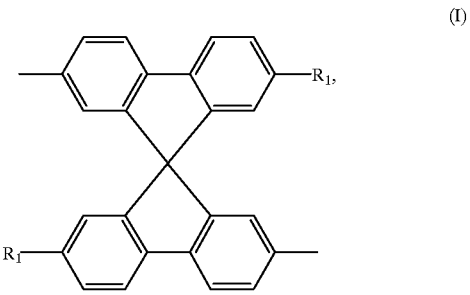

(I)

where
the two $R_1$s are, independently of one another, H, $C_1$–$C_{18}$alkyl, $C_6$–$C_{14}$aryl, $C_7$–$C_{15}$aralkyl, $C_1$–$C_{18}$alkoxy, $R_2$—(O—$C_nH_{2n}$)$_m$—O—, $C_1$–$C_{18}$alkylthio, $C_1$–$C_{18}$dialkylamino, —C(O)OH, —C(O)O—$C_1$–$C_{18}$alkyl, —C(O)—N($C_1$–$C_{18}$alkyl)$_2$, —SO$_3$H, —SO$_3$—$C_1$–$C_{18}$alkyl, —SO$_2$—N($C_1$–$C_{18}$alkyl)$_2$, $C_1$–$C_{17}$alkyl-C(O)—O— or $C_1$–$C_{17}$alkyl-C(O)—, $R_2$ is H or $C_1$–$C_{12}$alkyl, n is from 2 to 6 and m is from 1 to 12.

The polymers can be used either alone or in admixture with at least one additional fluorophore whose absorption band overlaps the emission band (fluorescent emission) of the polymer of the formula I as active radiative layer for light-emitting diodes, VDUs and display elements.

8 Claims, No Drawings

POLY(9,9'-SPIROBISFLUORENES), THEIR PRODUCTION AND THEIR USE

This application is a continuation of Ser. No. 09/077,484 filed May 29, 1998, now U.S. Pat. No. 6,132,641, which is a 371 of PCT/EP96/05091 filed Nov. 19, 1996.

The present invention relates to unsubstituted and substituted poly(9,9'-spirobisfluorenes); a process for their preparation; a composition comprising a support material and a layer of an unsubstituted or substituted poly(9,9'-spirobisfluorene), which may, if desired, further comprise a luminophore; a composition comprising an unsubstituted or substituted poly(9,9'-spirobisfluorene) which comprises a luminophore; and the use of the compositions or the poly (9,9'-spirobisfluorenes) as fluorophores, for example in light-emitting diodes or electrodes in display applications, and also 2,2'-dihalo-7,7'-disubstituted 9,9'-bisfluorenes.

In recent times, materials which emit fluorescent radiation have attracted greatly increased interest for display elements or photodiodes. In Adv. Mater. 1994, 6, No. 3, pages 190 to 198, J. M. Tour describes polyphenylenes which are known to emit blue fluorescent light. The good mechanical and thermal properties of the polyphenylenes are known. The insolubility in organic solvents and the associated unsatisfactory processibility and also the instability of doped polyphenylenes greatly impairs commercial utilization. There is a great need for blue-fluorescing and processible materials based on aromatic hydrocarbons, which materials have excellent thermal and mechanical properties (for example thermal stabilities above 200° C.); the polymers should be able to be prepared easily and, in particular, the targeted preparation of defined polymers should be possible. Furthermore, it is desirable for the polymers to be suitable as matrix for the incorporation of small amounts of different fluorophores in order to obtain fluorescent emissions over the entire visible spectrum.

It has now surprisingly been found that 9,9'-bisfluorenes can be polymerized to give blue-fluorescing polymers which are soluble in many solvents and are therefore also readily processible, for example by means of customary coating processes. The polymers have excellent thermal and mechanical stabilities and are excellent matrix systems for the incorporation of molecular fluorophores which can be used in fluorescent displays and in electroluminescent displays.

The invention provides, firstly, soluble poly(bis-9,9'-fluorenes) comprising identical or different structural repeating units of the formula I,

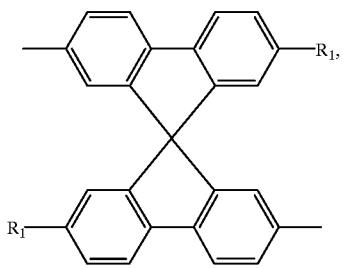

(I)

where
the two $R_1$s are, independently of one another, H, $C_1$-$C_{18}$alkyl, $C_6$-$C_{14}$aryl, $C_7$-$C_{15}$aralkyl, $C_1$-$C_{18}$alkoxy, $R_2$—(O—$C_nH_{2n}$)$_m$—O—, $C_1$-$C_{18}$alkylthio, $C_1$-$C_{18}$dialkylamino, —C(O)OH, —C(O)O—$C_1$-$C_{18}$alkyl, —C(O)—N($C_1$-$C_{18}$alkyl)$_2$, —SO$_3$H, —SO$_3$—$C_1$-$C_{18}$alkyl, —SO$_2$—N($C_1$-$C_{18}$alkyl)$_2$, $C_1$-$C_{17}$alkyl -C(O)—O— or $C_1$-$C_{17}$alkyl-C(O)—, $R_2$ is H or $C_1$-$C_{12}$alkyl, n is from 2 to 6 and m is from 1 to 12.

The alkyl groups in alkyl, alkoxy, alkylthio, diaminoalkyl, carboxylic ester or sulfonic ester, carboxamide or sulfonamide, alkyl-CO$_2$— and alkyl-C(O)— radicals $R_1$ can be linear or branched and preferably contain from 1 to 12, particularly preferably from 1 to 8, C atoms. Some examples of alkyl are methyl, ethyl, n- and i-propyl, n-, i- and t-butyl, and the isomers of pentyl, hexyl, heptyl, octyl, nonyl, decyl, undecyl, dodecyl, tetradecyl, hexadecyl and octadecyl.

Aryl radicals $R_1$ preferably contain from 6 to 10 C atoms. Some examples are naphthyl, biphenylyl and, particularly preferably, phenyl.

Aralkyl radicals $R_1$ preferably contain from 7 to 12 C atoms and the alkylene group in the aralkyl radical preferably contains 1 or 2 C atoms. A preferred example is benzyl and also phenylethyl.

Halogen atoms $R_1$ are preferably F, Cl or Br.

Alkyl radicals $R_2$ preferably contain from 1 to 8 and particularly preferably from 1 to 4 C atoms. They can be linear or branched. Some examples are methyl, ethyl, n-propyl and n-butyl.

In the radical $R_2$—(O—$C_nH_{2n}$)$_m$—O—, n is preferably from 2 to 4, particularly preferably 2 or 3.

In the radical $R_2$—(O—$C_nH_{2n}$)$_m$—O—, m is preferably from 1 to 8, particularly preferably from 1 to 6.

In a preferred embodiment of the invention, the two $R_1$s in the polymers of the formula I are identical radicals as defined above.

In a preferred embodiment of the invention, each $R_1$ in the polymers of the formula I is H, $C_1$-$C_{12}$alkyl-C(O)— or $C_1$-$C_{12}$alkoxy.

The polymers of the invention can be crosslinked, which depends essentially on the method of preparation. The degree of crosslinking can be so high that a virtually only crosslinked low molecular weight polymer, which is, however, still soluble, is obtained. Such polymers comprise structural units of the formula Ia, Ib or both structural units,

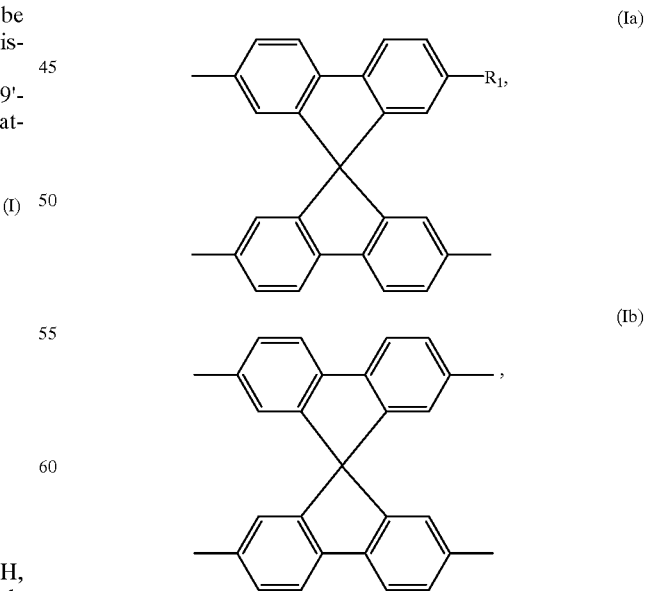

where $R_1$ is as defined above.

Structural units of the formula Ia are formed from monosubstituted 9,9'-bisfluorenes and structural units of the formula Ib are formed from unsubstituted 9,9'-bisfluorene.

The degree of polymerization (number of structural repeating units) can be from 2 to 100, more preferably from 3 to 50, even more preferably from 3 to 40 and particularly preferably from 5 to 30. The term polymers thus also encompasses oligomers. In general, the polymers of the invention comprise polymer chains having different degrees of polymerization (chain lengths).

The polymers of the invention can be prepared by methods known per se and by methods analogous to those described in the literature.

The invention further provides a process for preparing poly(bis-9,9'-fluorenes) comprising identical or different structural repeating units of the formula I,

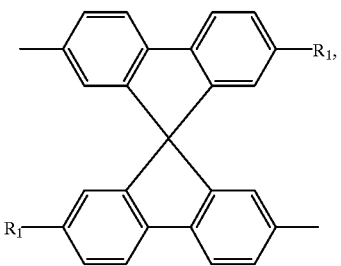

(I)

and, if desired, identical or different structural units of the formulae

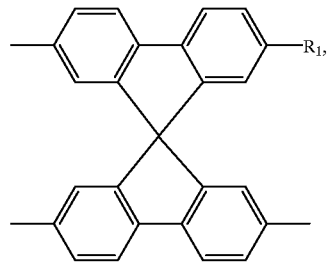

(Ia)

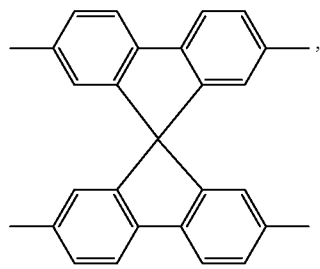

(Ib)

where $R_1$ is as defined above, which process comprises cationically-oxidatively polymerizing a) at least one halogen-free 9,9'-bisfluorene of the formula II,

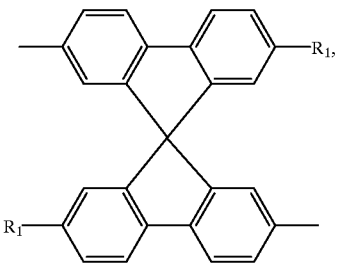

(II)

where $R_1$ is as defined above,
in the presence of an inert solvent.

Examples of suitable solvents are N,N-disubstituted carboxamides and N-substituted lactams (dimethylformamide, N-methylpyrrolidone), esters (butyl acetate), ethers (dibutyl ether), sulfoxides (dimethyl sulfoxide), sulfones (tetramethylene sulfone), aliphatic and aromatic hydrocarbons (toluene, xylene), halogenated or nitrated aliphatic and aromatic hydrocarbons (carbon tetrachloride, tetrachloroethane) and carbon disulfide.

The cationic-oxidative polymerization has been described for benzene by P. Kovacic et al. in Tetrahedron Letters No. 11, pages 467 to 469 (1962) and can also be employed analogously for the polymerization of 9,9'-spirobisfluorenes.

The polymerization is carried out, for example, using oxidizing Lewis acids such as $FeCl_3$ or using Lewis acids, mainly metal halides such as $AlCl_3$, $AlBr_3$, $BF_3$ or $BCl_3$, in combination with an oxidizing agent such as a metal compound having a relatively high oxidation state. Use is frequently made of $CuCl_2$. Oxidizing agents such as $KMnO_4$, $Fe^{+3}$ salts and benzoquinone derivatives such as tetrachlorobenzoquinone can also be used. It is also possible to employ electrochemical oxidation in a suitable organic solvent for effecting the polymerization.

The molar ratio of spirobisfluorene to catalyst or Lewis acid can be from 1:0.2 to 1:2, preferably from 1:0.4 to 1:1.5 and particularly preferably from 1:0.5 to 1:1.2. The molar ratio of Lewis acid to oxidizing agent can be, for example, from 1:0.2 to 1:1, preferably from 1:0.3 to 1:0.8 and particularly preferably from 1:0.4 to 1:0.6.

The reaction temperature is preferably from 200° C. to 200° C., more preferably from 20° C. to 150° C., particularly preferably from 20° C. to 100° C. and most particularly preferably from 30° C. to 80° C.

The reaction can be carried out, for example, by adding the catalyst to the dissolved spirobisfluorene, if desired heating the mixture and allowing it to react for some time (for example up to 24 hours) while stirring. The polymer formed can then be precipitated and filtered off or the solvent can be removed. To remove the Lewis acids/oxidizing agents, the residues can be washed with water, dried and then treated with solvents such as methylene chloride or tetrahydrofuran to isolate the desired soluble polymers.

In this polymerization method, crosslinked polymers are frequently formed and insoluble polymers can easily be removed. The degree of crosslinking can be influenced by the reaction conditions, for example the monomer concentration in the reaction mixture, the amount of catalyst and the ratio of catalyst to oxidizing agent, and by the reaction temperature.

Another way of preparing the polymers of the invention is from 2,2'-halogenated 9,9'-spirobisfluorenes using a method similar to that described by T. Yamamoto et al. in Bulletin of the Chemical Society of Japan, Vol. 51 (7), pages 2091 to 2097 (1978) and Macromolecules 25, pages 1214 to 1223 (1992). This method is preferred since polymers having a defined structure can be prepared in a targeted manner.

The invention also provides a process for preparing poly(bis-9,9'-fluorenes) comprising identical or different structural repeating units of the formula I,

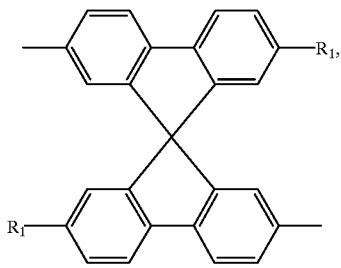

(I)

where $R_1$ is as defined above, which process comprises reacting a 2,2'-dihalo-9,9'-spirobisfluorene of the formula III,

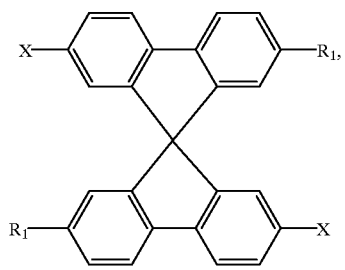

(III)

where $R_1$ is as defined above and X is halogen, in the presence of an inert solvent, an alkali metal or alkaline earth metal and a transition metal complex or metal salt of a transition metal.

X is preferably F, Cl or Br, more preferably Cl or Br and particularly preferably Br.

Suitable solvents are mainly the solvents used for Grignard reactions, for example aromatic hydrocarbons such as benzene, toluene, xylene, nitrobenzene and ethers such as diethyl ether, dipropyl ether, dibutyl ether, tetrahydrofuran, dioxane, ethylene glycol diethyl ether, ethylene glycol dimethyl ether and diethylene glycol dimethyl ether.

As alkali metals and alkaline earth metals, use is frequently made of Li, Na, K, Zn, Cd, Mg and Ca; particular preference is given to Li and Mg.

A great many suitable transition metal complexes are known. The transition metal complexes can be those of metal ions or uncharged metals. Some examples of metals are Fe, Co, Ni, Mo, Cr, W and noble metals such as Pt, Pd, Ru, Ir and Os. In the case of metal ion complexes, the anions can be derived from inorganic or organic acids, for example acetic acid, benzoic acid, toluenesulfonic acid, sulfuric acid and hydrohalic acids. Preference is given to metal halide complexes. Examples of uncharged ligands are open-chain and cyclic 1,3-dienes (cyclohexadiene, cyclooctadiene), nitriles (acetonitrile and benzonitrile), ethers, alcohols, tertiary phosphines (triphenylphosphine and tricyclohexylphosphine), ditertiary diphosphines, tertiary amines and ditertiary diamines such as bipyridine. Some examples of metal complexes are Ni(cyclooctadiene)$_2$ in admixture with P(C$_6$H$_5$)$_3$, Ni[P(C$_6$H$_5$)$_3$]$_4$, NiCl$_2$(bipyridine)$_2$, NiBr$_2$[P(C$_6$H$_5$)$_3$]$_2$, Pd(Cl)$_2$(bipyridine)$_2$, NiCl$_2$, CoCl$_2$, FeCl$_2$ and FeCl$_3$.

The amount of alkali metals or alkaline earth metals is preferably equimolar to the amount of dihalo-9,9'-spirobisfluorene, but a slight excess can also be used. The amount of transition metal complexes or transition metal salts is preferably likewise equimolar, but a slight excess or deficiency can be used.

The reaction can take place even under mild conditions at room temperature. A higher temperature of, for example, up to 150° C., preferably up to 100° C., accelerates the reaction.

The polymerization can be carried out by combining the reaction components with the solvent, then heating the mixture and allowing it to react to completion. To avoid excessively long induction times, a small amount of elemental iodine, for example, can be added. The reaction can also be carried out by first preparing the corresponding organometallic compound (Grignard compound) from the dihalo-9,9'-spirobisfluorene and an alkali metal or alkaline earth metal or a corresponding metal alkyl and only then adding a transition metal complex.

The polymers can be isolated in a customary manner, for example by filtering off insoluble constituents of the reaction mixture, washing to remove salts, precipitation or removing the solvent. The polymers can be purified by reprecipitation and, if appropriate, washing.

Some of the compounds of the formula II are known or they can be prepared by methods known per se.

2,2'-Dibromo-9,9'-spirobisfluorene can be prepared by direct bromination of 9,9'-spirobisfluorene in the presence of Lewis acids such as FeBr$_3$ (V. Prelog et al., Helvetica Chimica Acta 52(5), page 4253 (1969). The resulting product mixtures of compounds having different degrees of bromination and positional isomers can be purified by recrystallization and chromatographic methods. 2,2'-Dinitro-9,9'-spirobisfluorene can be prepared by the method of J. Weissenburger, JACS, page 4253 (1950) and isolated in pure form from the product mixture by recrystallization and chromatographic methods. The dinitro compound can, for example, be reduced using iron in ethanol to give the diamine, then diazotized and reacted with CuBr to form 2,2'-dibromo-9,9'-spirobisfluorene.

2,2'-Diamino-9,9'-spirobisfluorene can be converted into the corresponding N,N,N',N'-tetraalkyl compounds by means of alkylating agents. The reaction of the dibromo compounds with organometallic hydrocarbon compounds (Grignard compounds) leads to the dialkyl or diaryl derivatives. Substitution with alcohols, thiols or polyoxaalkylenediol monoethers gives the alkoxy-, alkylthio- and polyoxaalkylenoxy-substituted derivatives.

Diazotized 2,2'-dinitro-9,9'-spirobisfluorene can be converted by means of concentrated sulfuric acid into 2,2'-dihydroxy-9,9'-spirobisfluorene which can be esterified in a manner known per se. 2,2'-Dimethyl-9,9'-spirobisfluorene can be oxidized in a customary manner to give the carboxylic acid and then esterified or amidated. 9,9'-Spirobisfluorene-2,2'-sulfonic acid is obtainable in a known manner by oxidation of 9,9'-spirobisfluorene-2,2'-dithiol, with the dithiol being obtainable by nucleophilic substitution of 2,2'-dibromo-9,9'-spirobisfluorene.

2,2'-Diacyl-9,9'-spirobisfluorenes can be obtained in a simple manner and in high yields by Friedel-Crafts acylation using carboxylic acid halides in the presence of Lewis acids such as AlCl$_3$.

It has surprisingly been found that the dihalo compounds of the formula III are obtained in high yields and regioselectivity from the compounds of the formula I in which $R_1$ is not a hydrogen atom if the reaction is carried out using elemental halogen, for example $Cl_2$, $Br_2$ or $I_2$, preferably $Br_2$, in the presence of an excess of a Lewis acid.

The invention further provides compounds of the formula IV,

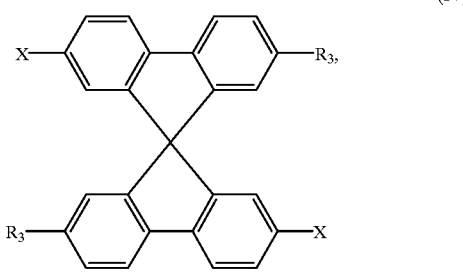

(IV)

where

X is halogen and $R_3$ is $C_1$-$C_{18}$alkyl, $C_6$-$C_{14}$aryl, $C_7$-$C_{15}$aralkyl, $C_1$-$C_{18}$alkoxy, $R_2$—(O—$C_nH_{2n}$)$_m$—O—, $C_1$-$C_{18}$alkylthio, $C_1$-$C_{18}$dialkylamino, —C(O)OH, —C(O)O—$C_1$-$C_{18}$alkyl, —C(O)—N($C_1$-$C_{18}$alkyl)$_2$, —SO$_3$H, —SO$_3$—$C_1$-$C_{18}$alkyl, —SO$_2$—N($C_1$-$C_{18}$alkyl)$_2$, $C_1$-$C_{17}$alkyl-C(O)—O— or $C_1$-$C_{17}$alkyl-C(O)—, $R_2$ is H or $C_1$-$C_{12}$alkyl, n is from 2 to 6 and m is from 1 to 12.

X is preferably Cl, Br or I, more preferably Cl or Br, and particularly preferably Br.

For $R_3$, the preferences and preferred embodiments given for $R_1$ in formula I apply.

The invention also provides a process for preparing the compounds of the formula IV, which comprises reacting a compound of the formula V,

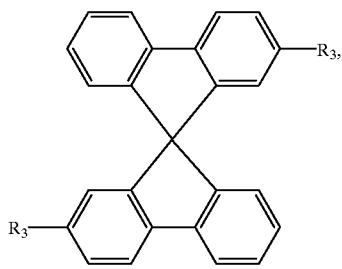

(V)

where $R_3$ is as defined above, in an inert solvent with elemental halogen in the presence of an excess of a Lewis acid.

The reaction temperature can be from room temperature to 200° C., preferably from 20 to 100° C. and particularly preferably from 20 to 50° C. The reaction is particularly preferably carried out at room temperature, which may require cooling at the beginning of the reaction.

The halogen is preferably used in equimolar amounts.

Suitable solvents are polar aprotic solvents which can be used alone or in mixtures. Some examples are open-chain or cyclic ethers, carbon disulfide and halogenated aliphatic or cycloaliphatic hydrocarbons.

Examples of suitable Lewis acids are $BF_3$, $BCl_3$, $AlBr_3$, $AlCl_3$, $ZnCl_2$, $ZnBr_2$, $FeCl_2$, $FeCl_3$, $FeBr_2$, $FeBr_3$, $TiCl_4$, $TiBr_4$, $SnCl_2$, $SnBr_2$, $SnCl_4$ and $SnBr_4$. Preference is given to using $AlCl_3$ or $AlBr_3$.

Excess can mean that the Lewis acids otherwise used in catalytic amounts in halogenation reactions of aromatics are present in an amount of at least 1 mol, preferably at least 2 mol, more preferably at least 4 mol and particularly preferably at least 10 mol, based on 1 mol of the compound of the formula V.

The isolation of the desired compounds and their purification can be carried out in a customary manner; purification itself is often not necessary since by-products are formed only in small amounts. The compounds of the invention are, depending on substitution, crystalline or amorphous solids which are soluble in polar aprotic solvents and are therefore readily processible. Even the monomers have a bluish fluorescence and are well suited to preparing defined and generally uncrosslinked polymers.

Despite the stiff structural units, the polymers of the invention are still soluble in customary organic solvents and can therefore be used and readily processed in solution as coating materials. They have very high thermal stabilities, glass transition temperatures and excellent mechanical properties. Furthermore, the poly(bis-9,9'-fluorenes) of the invention have absorption bands in the wavelength region below about 400 nm, and fluorescence emission maxima at wavelengths of from about 420 to 460 nm. They are thus blue-fluorescing materials which have been provided for the first time as processible polymers.

The invention further provides a composition comprising (a) a solvent and (b) a poly(bis-9,9'-fluorene) having identical or different structural repeating units of the formula I.

The amount of dissolved poly(bis-9,9'-fluorene) depends essentially on the solvent, the degree of polymerization and crosslinking and the substitution. The solutions according to the invention can contain from 0.01 to 80% by weight, preferably from 0.01 to 60% by weight, more preferably from 0.01 to 50% by weight, particularly preferably from 0.1 to 30% by weight and very particularly preferably from 0.1 to 20% by weight, of poly(bis-9,9'-fluorene), based on the total amount of the composition.

The composition of the present invention can comprise further additives, for example processing aids, agents for improving the mechanical and thermal properties, agents for improving the appearance or agents for improving the adhesion properties. Some examples are fluidizers, or adhesion promoters, dyes, pigments, heat stabilizers and light stabilizers, antistatics, antioxidants, lubricants, mold release agents, fillers, reinforcing fillers and viscosity-increasing substances.

In a particularly preferred embodiment, the composition of the invention (solution) further comprises at least one fluorescent dye (fluorophore). Preference is given to those fluorescent dyes whose absorption band overlaps the emission band (fluorescent emission) of the polymer of the invention. The amount of additional fluorescent dye can be, for example, from 0.000001 to 10% by weight, preferably from 0.00001 to 5% by weight, more preferably from 0.0001 to 3% by weight, particularly preferably from 0.001 to 3% by weight and very particularly preferably from 0.001 to 2% by weight, based on the amount of polymer. Many such dyes are known. Some examples are rhodamines, fluoresceins, cumarins, distyrylbiphenyls, stilbenes, phthalocyanines, naphthalocyanines, metal complexes of transition metals and lanthanide metals. It is also possible to use fluorescent latent pigments (solubilized pigments having solubilizing substituents such as detachable protective groups) selected from the group consisting of diketopyrrolopyrroles or quinacridones, fluorescent perylene derivatives or fluorescent perinones. It is likewise possible to use commerical products such as Lumogen L Yellow®, Brilliant Yellow®, Yellow Orange® or Red Orange® (BASF) and also 2,2'-dihydroxybipyridyls and related compounds. Molecularly dispersed (dissolved) fluorescent pigments can also be used. Such compositions are obtainable by dissolving pigments solubilized by means of protective groups in the polymer of the invention and subsequently splitting off the protective group, for example by heating.

The composition (solution) of the invention can be processed in molds with removal of the solvent, if desired with application of vacuum, to produce free-standing moldings and films. The polymers obtained can be doped with, for example, iodine or salts such as alkali metal hexafluorometalates and used as electric conductors, for example as electrodes. The solutions are of particular importance for coating support materials.

The invention furthermore provides a support material which is coated on at least one side with a polymer according to the invention.

In a preferred embodiment, the polymer layer comprises at least one further fluorophore dispersed homogeneously in the polymer layer; the emission band of the polymer preferably overlaps the absorption band of the fluorophore. By means of the content of additional fluorophores, all colors of the visible spectrum can be generated by selection of different emissions in the visible region, with the polymer itself having a blue fluorescence. This blue basic fluorescence can be reinforced by blue-emitting fluorophores or modified. The preferred amounts and some selected fluorophores have been indicated above.

A great number of support materials are known. The support material can be an inorganic or organic support material. The support material can be opaque, translucent or transparent. Preference is given to transparent support materials. Examples of suitable support materials are plastics, glass, cermics, minerals, rocks, metal oxides and metal mixed oxides, metal nitrides, metal carbides, semiconductors, transparent electric conductors (for example ITO-glass, glass supports coated with $SnO_2/In_2O_3$), metals and metal alloys.

The luminescence of the polymers of the invention and their mixtures with fluorophores can also be stimulated by electric conductors (electrofluorescence). A particularly advantageous embodiment of the invention is therefore an electroluminescent composition comprising an electric conductor as support material which is coated on at least one side with a polymer according to the invention either alone or in admixture with at least one additional fluorophore. The coating is preferably connected to a counterelectrode which is particularly preferably transparent.

The electric conductors can, depending on the application, be opaque, translucent or transparent and be semiconductors or metallic conductors. Transparent conductors are preferably glasses coated with semiconducting metal oxides or mixtures of metal oxides.

The thickness of the polymer layer can be, for example, from 0.1 to 1000 μm, preferably from 1 to 500 μm and particularly preferably from 10 to 200 μm.

The coated support material can be produced in a manner known per se by dipping, painting or casting processes, particularly spin coating, with the thickness of the layer being able to be determined by means of the content of polymer and, if used, fluorophore in the solution and also by selection of the process conditions.

The polymers and coated support materials of the invention can be used wherever markings by means of fluorophores are to be detected or decorative effects are to be achieved. The coated electric conductors can be used particularly advantageously as light-emitting diodes for the entire visible spectrum. Transparent, coated electrodes are also suitable for VDUs or display elements of electronic image reproduction systems.

The invention further provides for the use of the polymers, if desired additionally doped with at least one further fluorophore, of the invention as active radiative layer for light-emitting diodes, VDUs and display elements.

The following examples illustrate the invention.

A) PREPARATION OF 9,9'-SPIROBISFLUORENES

Example A1

Preparation of 2,2'-dibromo-9,9'-spirobisfluorene

A solution of 0.7 g of 2,2'-diamino-9,9'-spirobisfluorene in 90 ml of half-concentrated aqueous HBr is stirred at from 0 to ° C. with 0.338 g of $NaNO_2$ in 20 ml of water for one hour and the excess sodium nitrite is then destroyed using urea. Subsequently, at 0° C., a solution of 0.701 g of CuBr in 50 ml of half-concentrated aqueous HBr is added and the mixture is stirred for two days at room temperature. The product which has precipitated is filtered off, washed with 2N aqueous NaOH and then with water. Reprecipitation from methanol gives the title compound in a yield of 47%.

$^1$H-NMR (400 Mhz, $CDCl_3$, TMS): 7.81 (d, J=7.6 Hz, 2H, 3-H); 7.70 (d, J=8.2 Hz, 2H, 4-H); 7.50 (dd, J=8.2 and 1.8 Hz, 2H, 3-H); 7.38 (td, J=7.6 Hz and 0.9, 2H, 6-H); 7.14 (td, J=7,6 and 0.9 Hz, 2H, 7-H); 6.84 (sd, J=1.8 Hz, 2H, 1-H); 6.71 (d, J=7.6, 2H, 8-H).

Example A2

Preparation of 2,2'-dihydroxy-9,9'-spirobisfluorene

A solution of 0.7 9 of 2,2'diamino-9,9'-spirobisfluorene in 70 ml of half-concentrated sulfuric acid is admixed at from 0 to 5° C. with a solution of 0.337 c of $NaNO_2$ in 20 ml of water and the mixture is stirred for one hour. The reaction solution is added to 40 ml of concentrated sulfuric acid and stirred under reflux for one hour. The precipitate is filtered off and washed with water, giving the title compound in a yield of 74%.

Example A3

Preparation of 2,2'-dihexanoyl-9,9'-spirobisfluorene

A solution of 31.6 mmol of 9,9'-spirobisfluorene is added to a suspension of 79.1 mmol of finely divided $AlCl_3$ and 69.9 mmol of hexanoyl chloride in 100 Ml Of $CS_2$. The mixture is stirred for one hour at room temperature and then poured into 40 ml of ice-cold water. The mixture is acidified with hydrochloric acid and the two phases are separated. The aqueous phase is extracted once with methylene chloride. The combined organic phases are then washed with water and dried over anhydrous potassium carbonate. The solvent is then evaporated and the title compound having a melting point of 142° C. is obtained in quantitative yield. Elemental analysis [found (theoretical)]: C, 86.51% (86.68); H, 7.04% (7.08); O, 6.25% (6.24).

Example A4

Preparation of 2,2'-dibromo-7,7'-dihexanoyl-9,9'-spirobisfluorene

A solution of 28.5 mmol of 2,2'-dihexanoyl-9,9'-spirobisfluorene in 50 ml of $CS_2$ is slowly added to a stirred suspension of 0.171 mmol of finely divided $AlCl_3$ in 100 ml of $CS_2$ and the mixture is then refluxed for one hour. The reaction solution is cooled and 57 mmol of bromine in 50 ml of $CS_2$ are then added. The mixture is stirred overnight at room temperature with exclusion of light. The reaction mixture is then poured onto a mixture of 300 ml of ice and 30 ml of hydrochloric acid and the phases are separated. The aqueous phase is washed twice with 200 ml of $CS_2$. The combined organic phases are washed with 300 ml of five percent aqueous sodium bicarbonate solution and then dried over $Na_2SO_4$. Evaporation of the solvent gives the title compound in a yield of 95%. Elemental analysis [found (theoretical)]: C, 64.98% (66.28); H, 4.87% (5.11); Br, 25.33% (23.83) O, 4.48% (4.77).

B) PREPARATION OF POLYMERS

Example B1–B4

Direct polymerization of 9,9'-spirobisfluorene (SBF)

1 Mol of 9,9'-spirobisfluorene is polymerized at 30° C. in $CS_2$ using $AlCl_3$/CuCl. Further information may be found in Table 1. PSBF is poly(9,9'-spirobisfluorene). The polymers are amorphous and light brown, blue-fluorescing solids. When analyzed by GPC using polystyrene as standard, the polymer of Example B2 gives an $M_n$ of 2684 and an $M_w$ of 16 516. A degree of polymerization of up to 15 is found by MALDI-MS analysis. The polymer B1 softens at 349° C. and decomposes at 434° C. The other data determined by differential thermal analysis are shown in Table 2.

TABLE 1

| Example | $AlCl_3$ (mol) | CuCl (mol) | Reaction time (h) | Proportion of cross-linked polymer (% of PSBF) | Proportion of polymer soluble in $CH_2Cl_2$ (% of PSBF) | Total yield (%) |
| --- | --- | --- | --- | --- | --- | --- |
| B1 | 0.5 | 0.25 | 2 | 23 | 77 | 13 |
| B2 | 1.0 | 0.5 | 12 | 18 | 82 | 19 |
| B3 | 1.2 | 0.6 | 2 | 59 | 59 | 11 |
| B4 | 2 | 1.35 | 24 | 98 | 2 | 43 |

TABLE 2

| Polymer from Example | Decomposition temperature (° C.) | 5% weight loss at |
| --- | --- | --- |
| B2 | 426 | 550 |
| B3 | 414 | 640 (10%) |
| B4 | 421 | 657 |

Example B5

Polymerization of 2,2'-dibromo-9,9'-spirobisfluorene

1 g (2.11 mmol) of 2,2'-dibromo-9,9'-spirobisfluorene together with 394 mg (2.53 mmol) of bipyridyl, 228 mg (2.11 mmol) of cyclooctadiene (COD) and 422 mg (2.53 mmol) of $Ni(COD)_2$ are dispersed in 20 ml of dimethylformamide (DMF). This dispersion is heated to 60° C. under inert gas (argon) and stirred at this temperature for 5 days. The polymer formed is precipitated in methanol acidified with HCl (100–150 ml), filtered, washed with methanol, dilute hydrochloric acid and water and subsequently dried at 50° C. in vacuo. This gives 0.605 g (91% of theory) of a blue-fluorescing polymer which is soluble in tetrahydrofuran, DMF and $CH_2Cl_2$. MALDI-MS analysis indicates a degree of polymerization of about 12. GPC analysis using polystyrene as standard indicates an $M_n$ of 2264 and an $M_w$ of 9213.

Example B6

Polymerization of 2,2'-dibromo-7,7'-dihexanoyl-9,9-spirobisfluorene

1 g (1.47 mmol) of 2,2'-dibromo-7,7'-dihexanoyl-9,9'-spirobisfluorene together with 274 mg (1.76 mmol) of bipyridyl, 158 mg (1.47 mmol) of COD and 293 mg (1.76 mmol) of $Ni(COD)_2$ are dispersed in 15 ml of DMF. The dispersion is heated to 70° C. and stirred at this temperature for 4 days under inert gas (argon). The further procedure is as described in Example B5. This gives 690 mg (90.5% of theory) of a blue-fluorescing polymer which is soluble in tetrahydrofuran, dimethylformamide and $CH_2Cl_2$. GPC analysis using polystyrene as standard indicates an $M_n$ of 3681 and an $M_w$ of 6306. The decomposition temperature of the polymer is 308° C. and the weight loss at 600° C. is 35%.

C) USE EXAMPLES

Example C1

The polymer from Example B2 or Example B5 is dissolved in $CH_2Cl_2$ and a 100 nm thick film on a quartz plate is produced by means of spin coating and the absorption and emission spectra are measured. In both cases, the absorption maximum is at $\lambda_{max}=370$ nm and the emission maximum is at $\lambda_{max}=420$ nm. To measure the emission spectrum, the specimen is irradiated at the absorption maximum (370 nm) and the radiation emitted is measured as a function of wavelength using an apparatus suitable for this purpose (fluorescence spectrometer).

Example C2

A film is produced as described in Example C1 from the polymer as described in Example B6. The absorption spectrum is broadened compared to Example C1 and has two absorption maxima at $\lambda_{max}=340$ and 355 nm. The emission maximum is at $\lambda_{max}=430$ nm.

Example C3

A film is produced as described in Example C1 from the polymer as described in Example B6, with 0.5% by weight of a fluorophore being additionally dissolved in the solution. The results are shown in Table 3.

TABLE 3

| Fluorophore | Absorption ($\lambda_{max}$) | Photoluminescence ($\lambda_{max}$) (emission maximum) |
|---|---|---|
| [structure: 7-diethylamino-3-(benzimidazol-2-yl)coumarin] | 437 | 503 |
| [structure: dicyanomethylene pyran with dimethylaminostyryl] | 480 | 565 |
| [structure: N-ethylpyridinium-distyryl-dimethylaniline BF$_4^-$] | 479 | 655 |

What is claimed is:

1. A compound of the formula IV,

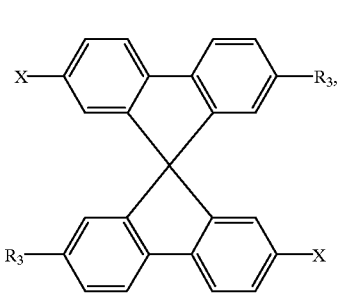

(IV)

where
  X is halogen and
  $R_3$ is $C_1$–$C_{18}$alkyl, $C_6$–$C_{14}$aryl, $C_7$–$C_{15}$aralkyl, $C_1$–$C_{11}$alkoxy, $C_{13}$–$C_{18}$alkoxy, $R_2$—(O—$C_nH_{2n}$)$_m$—O—, $C_1$–$C_{18}$alkylthio, $C_1$–$C_{18}$dialkylamino, —C(O)OH, —C(O)O—$C_1$–$C_{18}$alkyl, —C(O)—N($C_1$–$C_{18}$alkyl)$_2$, —SO$_3$H, —SO$_3$—$C_1$–$C_{18}$alkyl, —SO$_2$—N($C_1$–$C_{18}$alkyl)$_2$, $C_2$–$C_{17}$alkyl-C(O)—O— or $C_2$–$C_{17}$alkyl-C(O)—, $R_2$ is H or $C_1$–$C_{12}$alkyl, n is from 2 to 6 and m is from 1 to 12.

2. A compound according to claim 1, wherein X is Cl or Br.

3. A process for preparing compounds of the formula IV according to claim 1, which comprises reacting a compound of the formula V,

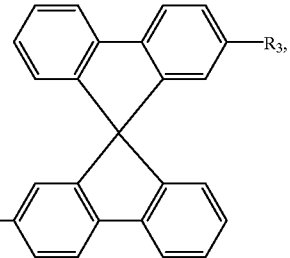

(V)

where $R_3$ is as defined in claim 1, in an inert solvent with elemental halogen in the presence of an excess of a Lewis acid.

4. A process according to claim 3, wherein the reaction temperature is from room temperature to 200° C.

5. A process according to claim 3, wherein the halogen is used in equimolar amounts.

6. A process according to claim 3, wherein the Lewis acid is BF$_3$, BCl$_3$, AlBr$_3$, AlCl$_3$, ZnCl$_2$, ZnBr$_2$, FeCl$_2$, FeCl$_3$, FeBr$_2$, FeBr$_3$, TiCl$_4$, TiBr$_4$, SnCl$_2$, SnBr$_2$, SnCl$_4$ or SnBr$_4$.

7. A process according to claim 3, wherein the Lewis acid is used in an amount of at least 1 mol per 1 mol of the compound of the formula V.

8. A process according to claim 7, wherein the Lewis acid is used in an amount of at least 4 mol.

* * * * *